the growth of various tumors in rodents, for example, Walker 256 carcinosarcoma and Lewis Lung carcinoma.

United States Patent [19]

Kawaguchi et al.

[11] 4,051,237
[45] Sept. 27, 1977

[54] GLYCOPEPTIDE ANTIBIOTICS BU-2231 A AND B AND PROCESS FOR PRODUCING SAME

[75] Inventors: Hiroshi Kawaguchi, Tokyo; Koji Tomita, Kawasaki; Hiroshi Tsukiura, Mitaka; Masataka Konishi, Yokohama, all of Japan

[73] Assignee: Bristol-Myers Company, New York, N.Y.

[21] Appl. No.: 608,494

[22] Filed: Aug. 28, 1975

[51] Int. Cl.² .............................................. A61K 35/74
[52] U.S. Cl. .................................. 424/117; 195/80 R; 424/124
[58] Field of Search .................... 424/117; 195/80 R

[56] References Cited

U.S. PATENT DOCUMENTS 3,681,491  8/1972  Umezawa et al. ................... 424/115

OTHER PUBLICATIONS

Umezawa et al., J. Antibiotic, Ser. A., Sept. 1966, pp. 200–209.
Umezawa et al., J. Antibiotic, Ser. A., Sept. 1966, pp. 210–215.

*Primary Examiner*—Jerome D. Goldberg
*Attorney, Agent, or Firm*—David M. Morse

[57] ABSTRACT

A novel water-soluble basic glycopeptide antibiotic complex designated herein as Bu-2231 is produced by fermentation of a Bu-2231-producing strain of *Streptoalloteichus hindustanus*. Complex Bu-2231 and two of its major components designated herein as Bu-2231 A and B are found to inhibit the growth of various Gram-positive and Gram-negative and acid-fast bacteria as well as certain plant pathogens. The complex and components Bu-2231 A and B are also useful in inhibiting the growth of various tumors in rodents, for example, Walker 256 carcinosarcoma and Lewis Lung carcinoma.

15 Claims, 4 Drawing Figures

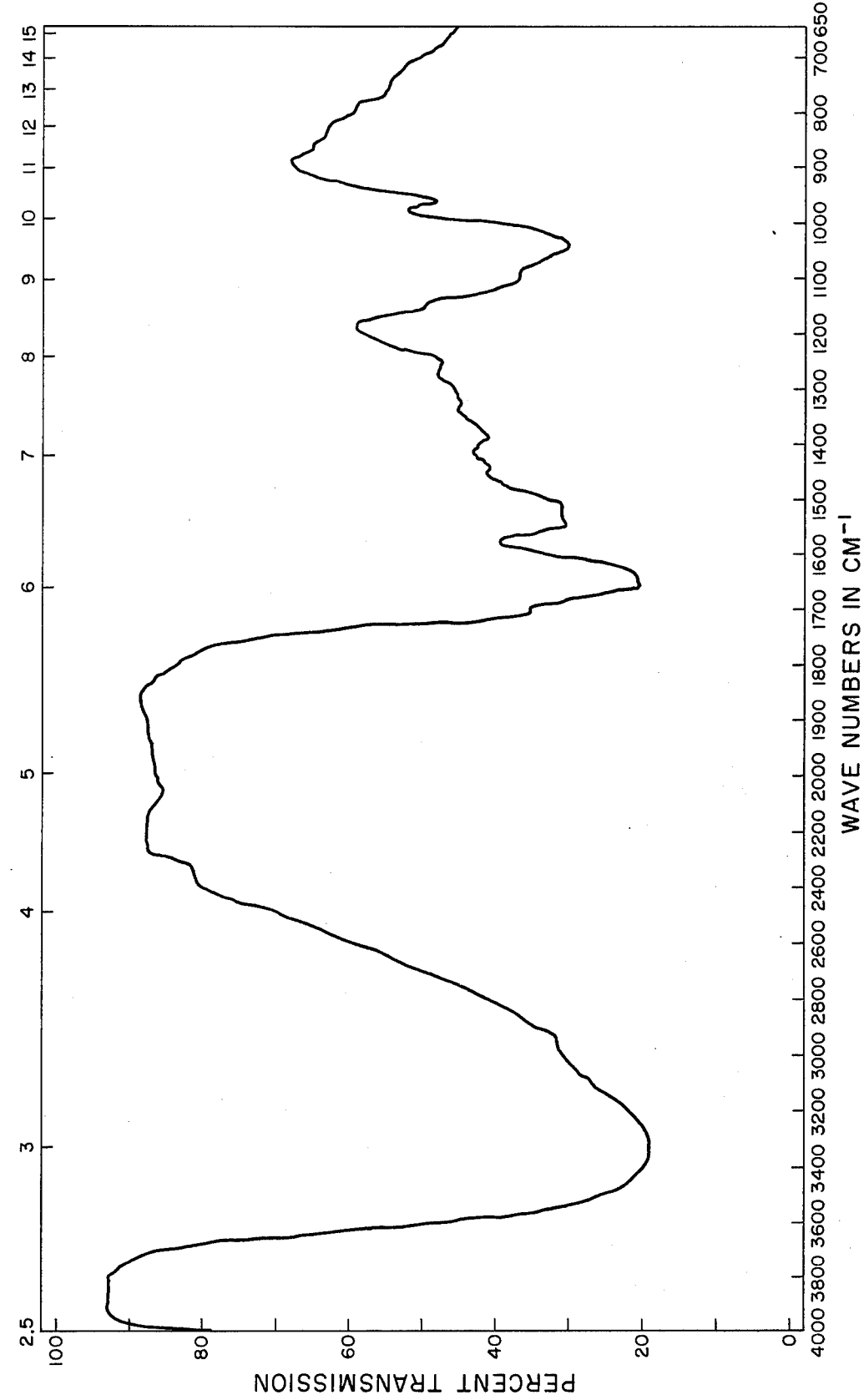

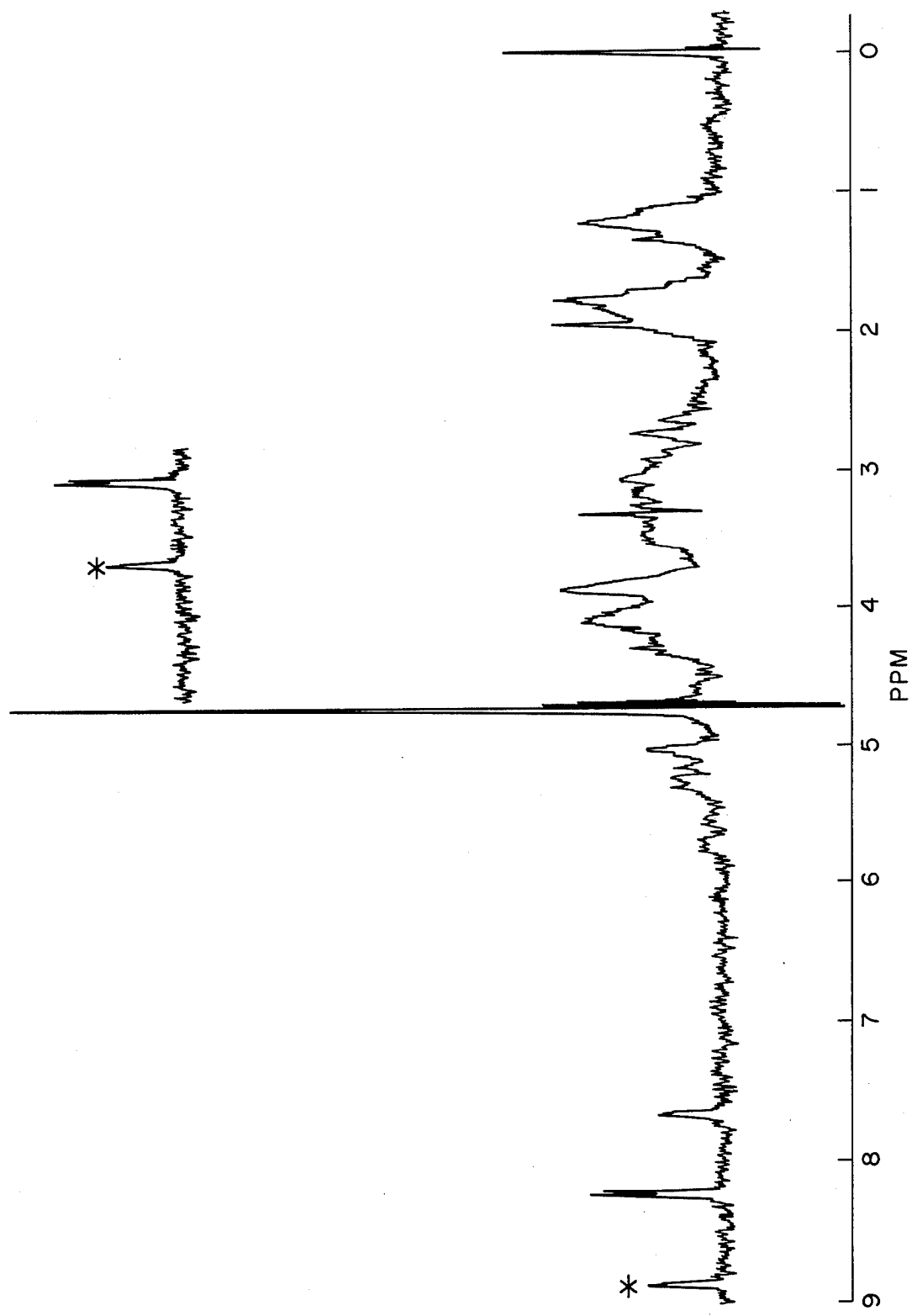
FIG. 2 NUCLEAR MAGNETIC RESONANCE SPECTRUM OF Bu-2231 A HYDROCHLORIDE IN $D_2O$

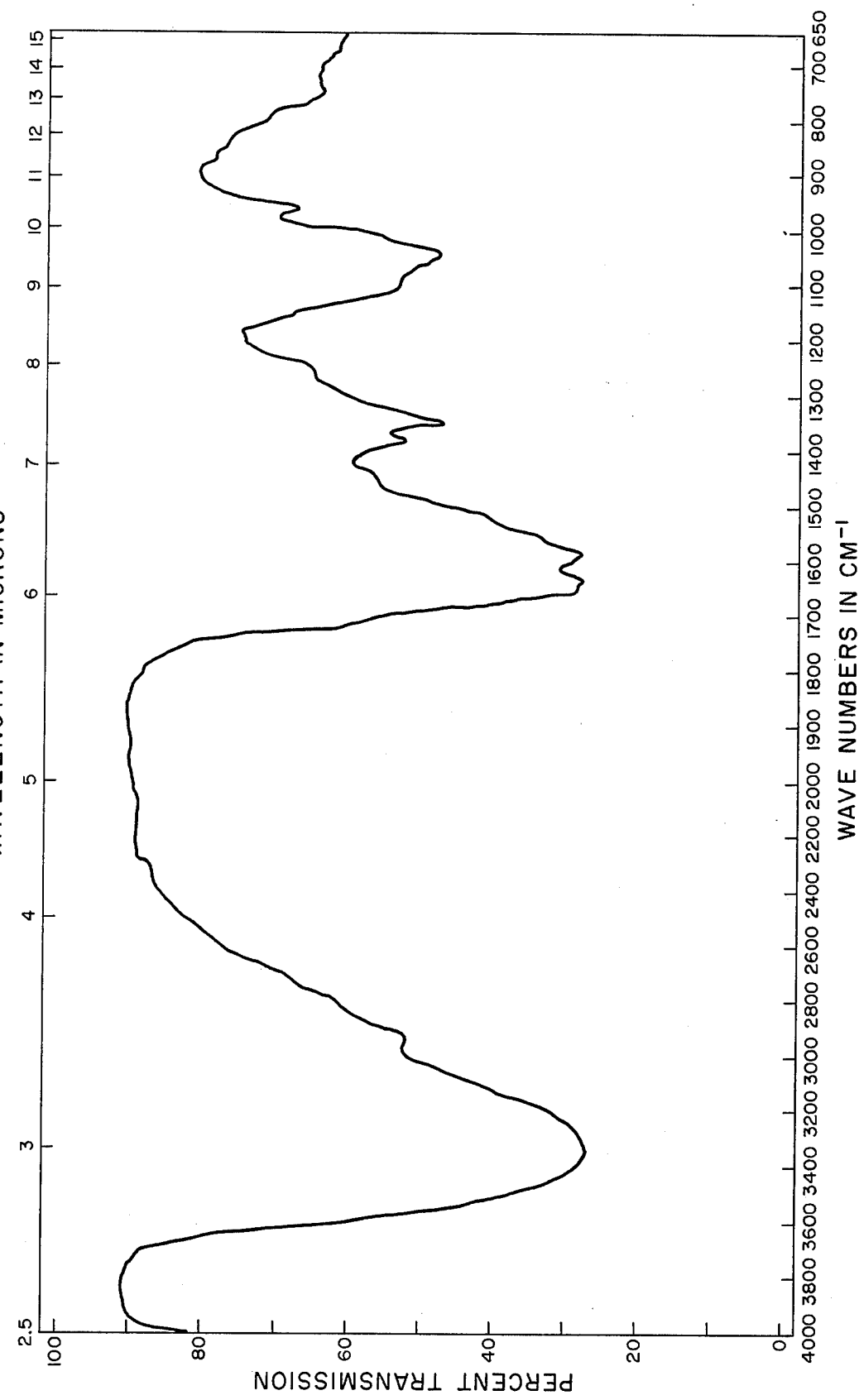

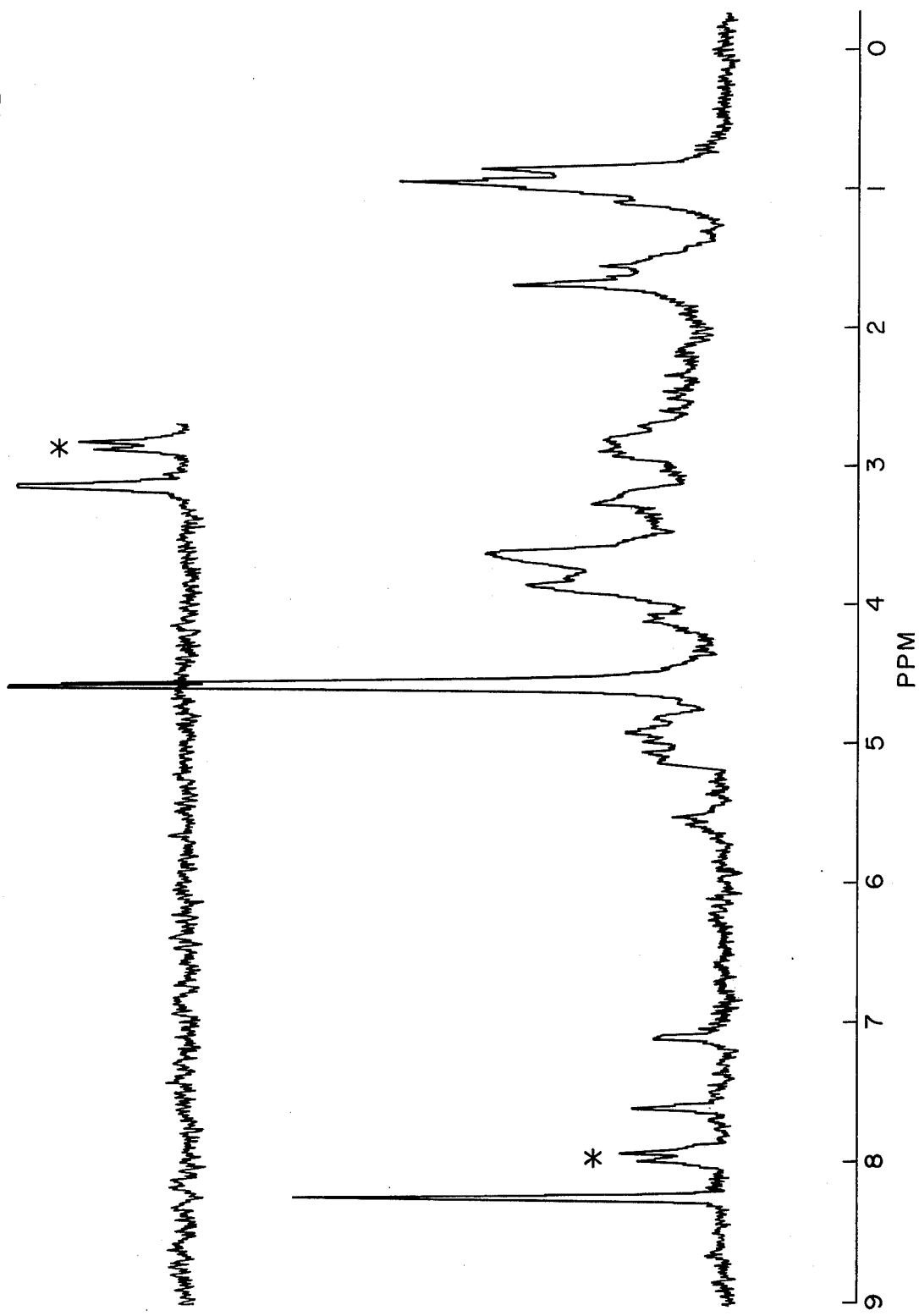
FIG. 4 NUCLEAR MAGNETIC RESONANCE SPECTRUM OF Bu-2231 B FORMATE IN $D_2O$

GLYCOPEPTIDE ANTIBIOTICS BU-2231 A AND B AND PROCESS FOR PRODUCING SAME

BACKGROUND OF THE INVENTION

1. Field of the invention

This invention relates to a new glycopeptide antibiotic complex and to its production, recovery and separation into two bioactive components.

2. Description of the prior art

Although a number of glycopeptide antibiotics have been discovered, some of which are also effective in inhibiting the growth of tumors in lower animals and man, there remains a need for additional antimicrobial and antitumor agents. A brief summary of the more important glycopeptide antibiotics is provided below.

The bleomycins are water-soluble basic glycopeptides produced from Streptomyces verticillus. They were first discovered by Umezawa et al. in 1966 and reported in J. Antibiotics, 19A, 200 (1966); see also U.S. Pat. No. 3,681,491. The bleomycin complex has been separated into several components including bleomycin A, $A_1$, $A_5$ and $B_2$. Bleomycin complex is presently being marketed for treatment of various neoplasms in man including squamous cell carcinoma, lymphosarcoma, reticulum cell sarcoma, testicular carcinoma and Hodgkin's disease.

The phleomycin group of antibiotics obtained from another strain of Streptomyces verticillus have been disclosed by Maeda et al. in J. Antibiotics: Vol. A9, pg. 82–85 (1956); Vol. A12, pg, 111 (1959); Vol. A12, pg. 285–289 (1959) and Vol. A17, pg. 194–199 (1964). As with bleomycin complex, phleomycin has been separated into a number of components which can exist in both a copper-free and a copper-complex form.

Zorbamycin and its related antibiotics zorbonomycin B and zorbonomycin C are reported in J. Antibiotics, 24(8), 543–557 (1971) and in British Pat. No. 1,277,150. These antibiotics isolated from fermentations of Streptomyces bikiniensis var. zorbonensis are closely related to the bleomycin and phleomycin families of antibiotics.

Another family of phleomycin-bleomycin group antibiotics was isolated from the culture broth of a variant of Streptomyces humidus and given the name YA-56. A description of the YA-56 complex and active components YA-56X and Y appears in J. Antibiotics, 24(10), 727–731 (1971) and in J. Antibiotics, 26, 77–83 (1973).

The antibiotic complex XK 49 and its main component victomycin (also called XK 49-1-B-2) are reported in J. Antibiotics, 28, 358–371 (1975). Victomycin was isolated from a sporangia-forming actinomycete, Streptosporangium violaceochromogenes MK 49 and appears to be similar to the bleomycins and zorbonomycin B.

The platomycins, a still further group of phleomycin-bleomycin-like antibiotics, were disclosed by Nara et al. in West German Published Application No. 2,408,121. Platomycin complex and its components platomycin A and B were produced from another strain of Streptosporangium designated Streptosporangium violaceochromogenes MK 78.

SUMMARY OF THE INVENTION

There is provided by the present invention a new water-soluble basic glycopeptide antibiotic complex designated Bu-2231, said complex being prepared by cultivating a Bu-2231-producing strain of Streptoalloteichus hindustanus, most preferably the strain Streptoalloteichus hindustanus A.T.C.C. 31158 or a mutant thereof, in an aqueous nutrient medium containing assimilable sources of carbon and nitrogen under submerged aerobic conditions until a substantial amount of Bu-2231 complex is produced by said organism in said culture medium and, optionally, recovering the Bu-2231 complex from the culture medium.

The invention also provides a process for producing as separate substances the principal antibiotic components of the complex designated herein as Bu-2231 A and B, said process comprising adsorbing the Bu-2231 complex on a cationic ion-exchange resin, fractionally eluting the components from the adsorbent, and recovering the desired separated components. This invention provides the complex and individual components A and B in their copper complex and copper-free forms and as free bases or pharmaceutically acceptable acid addition salts thereof.

DESCRIPTION OF THE DRAWINGS

FIG. 1 shows the infrared absorption spectrum of Bu-2231 A in the form of its copper-free hydrochloride salt when pelleted in potassium bromide.

FIG. 2 shows the proton magnetic resonance spectrum of Bu-2231 A as the copper-free hydrochloride salt dissolved in $D_2O$ using 2,2-dimethyl-2-silapentane-5-sulfonate (DSS) as the internal standard as determined with a JEO1 60 MHz NMR spectrometer (type TNM-C-60 HL).

FIG. 3 shows the infrared absorption spectrum of Bu-2231 B in the form of its copper-free formate salt when pelleted in potassium bromide.

FIG. 4 shows the proton magnetic resonance spectrum of Bu-2231 B as the copper-free formate salt dissolved in $D_2O$ using 2,2-dimethyl-2-silapentane-5-sulfonate (DSS) as the internal standard as determined with a JEO1 60 MHz NMR spectrometer (type TNM-C-60 HL).

DETAILED DESCRIPTION

This invention relates to a novel water-soluble basic glycopeptide antibiotic complex designated herein as Bu-2231 and to its preparation by fermentation of a new strain of Streptoalloteichus designated strain E465-94 in the Bristol-Banyu culture collection. The above organism is an actinomycetes bacterium which was isolated from an Indian soil sample. A culture of the organism has been deposited in the American Type Culture Collection, Washington, D.C., and added to its permanent collection of microorganisms as A.T.C.C. 31158.

The novel glycopeptide complex of this invention comprises two principal glycopeptide components designated Bu-2231 A and B, both of such components being bioactive. The complex and each of the above-mentioned components have an inhibitory action against the growth of microbial organisms, both bacteria and fungi, which are pathogenic to animal and plant life, and said antibiotics are therefore useful for therapy against bacterial infection in man or animals and for prevention or suppression of diseases of rice, pea, wheat or other plants caused by plant-pathogenic organisms. The complex and individual components are also useful in treating various tumor systems in rodents including Walker 256 carcinosarcoma (ascitic form) and Lewis Lung carcinoma.

The Microorganism

The morphological, cultural and physiological characteristics of strain E465-94 are summarized below:

Morphology

Strain E465-94 produces cluster and scleroium in the aerial mycelium on most agar media. The cluster is a dominant spore forming structure, and the formation of sclerotia is somewhat capricious. The cluster consists of curved or L-shaped short spore-chains with many branches and often develops into a thick mass. Some spore-chains protrude from the cluster structure and often form open spirals. The shape of the sclerotium is oval or occasionally irregular. The fragmentation of vegetative mycelium does not occur. Whorl is not formed.

Cultural and Physiological Characteristics

Strain E465-94 produces abundant aerial mycelia on most of the agar media tested. The color of the mature aerial mycelium is light yellowish beige or pale pinkish yellow. Diffusible pigment is not produced. Tyrosinase reaction is negative. The strain is thermodurio and grows abundantly at 50° C. The cultural and physiological characteristics and the carbohydrate utilization of strain E465-94 are shown in Tables 1, 2 and 3.

Table 1.

| Cultural Characteristics of Strain E465-94 | | |
|---|---|---|
| Yeast extract-malt extract agar (ISP No. 2 medium) Pridham, et al., 1956-57 | G: | Abundant |
| | R: | Pale yellowish brown to light brown |
| | A: | Thick, velvety, light yellowish beige or pale pinkish beige |
| | D: | None |
| Oat meal agar (ISP No. 3 medium) Kuster, 1959 | G: | Moderate |
| | R: | Colorless, partially pale yellowish brown |
| | A: | Powdery to velvety occasionally with patches, pale pinkish beige |
| | D: | None |
| Inorganic salts-starch agar (ISP No. 4 medium) Kuster, 1959 | G: | Moderate |
| | R: | Colorless to pale yellowish brown |
| | A: | Powdery to velvety, pale pinkish yellow |
| | D: | None |
| Glycerol-asparagine agar (ISP No. 5 medium) Pridham and Lyons, 1961 | G: | Restricted |
| | R: | Colorless to pale olivaceous yellow |
| | A: | Powdery with patches, whitish to pale yellowish beige |
| | D: | None |
| Peptone-yeast extract-iron agar (ISP No. 6 medium) Tresner and Danga, 1958 | G: | Scant |
| | R: | Brown |
| | A: | Scant, white |
| | D: | Pale brown |
| Tyrosine agar (ISP No. 7 medium) Shinobu, 1958 | G: | Moderate |
| | R: | Pale yellow to pale greenish yellow |
| | A: | Velvety to cottony, white later light pinkish yellow |
| | D: | None |
| Bennett's agar | G: | Moderate |
| | R: | Pale olivaceous yellow to light brown |
| | A: | Velvety, light yellowish beige |
| | D: | None |
| Nutrient agar | G: | Restricted |
| | R: | Pale brownish yellow |
| | A: | Scant, white |
| | D: | Pale yellow |
| Soil extract agar | G: | Moderate |
| | R: | Colorless |
| | A: | Thin, pale yellowish beige, patches |
| | D: | None |
| Tomato paste-oat meal agar | G: | Moderate |
| | R: | Light yellowish brown |
| | A: | Velvety, pale pinkish yellow |

Table 1.-continued

| Cultural Characteristics of Strain E465-94 | |
|---|---|
| | D: None |

Abbreviation: G = Growth; R = Reverse color; A = Aerial mycelium; D = Diffusible pigment Table 2.

| Physiological Characteristics of Strain E465-94 | |
|---|---|
| Gelatin liquefaction | Positive; rapidly liquefied |
| Starch hydrolysis | Positive |
| Milk | Remarkable coagulation and slight peptonization. pH alkalinized. Yellowish ring growth. |
| Melanin from L-tyrosine | Negative tyrosinase |
| Nitrite from nitrate | Positive |
| Growth temperature | Abundant growth at 32-50° C., moderate at 25-30° C., restricted at 23° C. and 52° C., scant at 20° C. and 54° C., no growth at 12° C. and 56° C. |
| Fluorescent light | No distinct inhibition of aerial mycelium formation under 15W-fluorescent lamp for 14 days. |
| NaCl tolerance | Restricted growth and aerial mycelium formation in Leudemann's agar medium at 5% NaCl. No growth at 7% NaCl. |
| Potato plug acidity tolerance | Normal growth and aerial mycelium formation on Leudemann's potato plug test. |
| Catalase reaction | Positive |
| Oxidase | Negative |
| Antibiotics produced | Bu-2231 complex and nebramycin factors. |

Table 3.

| Carbohydrate-utilization of Strain E465-94 | | | |
|---|---|---|---|
| D(−)-arabinose | − | D(+)-melibiose | − |
| L(+)-arabinose | − | trehalose | ++ |
| D-xylose | − | raffinose | − |
| D-ribose | + | D(+)-melezitose | − |
| L-rhamnose | − | soluble starch | ++ |
| D-glucose | ++ | cellulose | − |
| D(+)-galactose | ++ | glycerol | ++ |
| D-fructose | ++ | inositol | − |
| D-mannose | ++ | D-mannitol | − |
| L(−)-sorbose | − | D-sorbitol | − |
| sucrose | ++ | dulcitol | − |
| lactose | ++ | salicin | − |
| cellobiose | − | | |

Basal medium: Pridham-Gottlieb salts medium, supplemented with 0.1%-Difco yeast extract.
Incubation temperature: 37° C.

Cell-wall Composition

The cell-wall preparation was carried out by the method described by T. Yamaguchi in J. Bacteriol. 89: 444-453 (1965). The amino acid analysis procedure was as follows: Purified cell-wall (10 mg.) was hydrolyzed in 1 ml. of 6N HCl in a sealed tube at 120° C. for 18 hours. The hydrolyzate was diluted with an equal volume of distilled water, filtered and then evaporated in vacuo to dryness. Half of the final product was redissolved in 0.1 ml. distilled water and examined by two-dimensional TLC. The other half was dissolved in 2 ml. of citrate buffer (pH 2.2) and analyzed by liquid chromatography. A 5 µl portion of the hydrolyzate was applied to a silica gel TLC plate (60F$_{254}$, E. Merck AG, Germany) and developed with phenol-water (4:1) in one direction and subsequently with n-butanol-acetic acid-water (3:1:1) perpendicularly to the first run. The spots were revealed by a spray of 0.2% ethanolic ninhydrin reagent, followed by heating the plate for 5 minutes at 110° C. In order to differentiate meso and/or DD-DAP from LL-LAP, 5 µl of the hydrolyzate was applied to a cellulose powder TLC plate. The plate was developed with the solvent system methanol-water-10N HCl-pyridine (80:17.5:2.5:10) for 24 hours and then sprayed with 0.2% ninhydrin reagent. In this TLC system, LL-DAP moved faster than the meso-DAP used as a reference standard. Amino acids in the cell-wall preparation were also determined by amino acid analyzer. The amino acid analysis of the cell-wall preparation of strain E465-94 showed the presence of meso-α,ε-diaminopimelic acid (meso-DAP), alanine and glutamic acid (Table 4). Carbohydrates in the cell-wall were determined as follows: A 50 mg. sample of the crude cell-wall was dissolved in 3 ml. of 2N $H_2SO_4$ and hydrolyzed in a sealed tube at 120° C. for 2 hours. The hydrolyzate was neutralized with saturated $Ba(OH)_2$ solution, the precipitated $BaSO_4$ removed by centrifugation and the supernatant fluid lyophilized. The material thus obtained was trimethylsilylated and the product subjected to gas chromatography and compared with various reference sugars. The carbohydrate analysis of the cell-wall of E465-94 indicated the presence of rhamnose, mannose, galactose and glucosamine (Table 5).

Table 4.

| Amino Acid Composition of Cell-Wall | | | | |
|---|---|---|---|---|
| DAP (isomer) | glycene | glutamic acid | aspartic acid | alanine |
| ++(meso) | ± | ++ | Trace | +++ |

Table 5.

| Carbohydrate Composition of Cell-Wall | | | | | |
|---|---|---|---|---|---|
| arabinose | rhamnose | mannose | galactose | glucose | glucosamine |
| − | + | ++ | +++ | − | ++ |

Comparison With Actinomycetes Strains Producing Bleomycin-type Antibiotics

Strain E465-94 produces a new antibiotic complex Bu-2231 which is believed to be composed of bleomycin-type antibiotics. Comparison was therefore made with several antinomycetes strains which have been reported to produce bleomycin or the bleomycin-related antibiotics. The results are summarized in Table 6. Strain E465-94 is clearly differentiated from any of these microorganisms.

Table 6.

| Name of microorganism | Comparison of Strain E465-94 with Six Actinomycetes Strains Producing Bleomycin Group Antibiotics | |
|---|---|---|
| | Antibiotic produced | Major difference from strain E465-94- |
| Streptomyces verticillus No. 843-1[1] | Phleomycins | Whorl formation. Positive utilization of inositol, mannitol, raffinose and rhamnose. Negative utilization of galactose. |
| Streptomyces verticillus B80-Z2[2] | Bleomycins | Whorl formation. Negative utilization of galactose, lactose and sucrose. |
| Streptomyces bikiniensis var. zorbonensis[3] | Zorbamycins | Aerial growth gray to grayish yellow. Sporophore straight Utilization ++: D-Xylose, L-arabinose, rhamnose, cellobiose. Utilization +: Raffinose, dulcitol, D-mannitol, D-sorbitol and inositol. |
| Streptomyces humidus var. antitumoris MCRL-0387[4] | YA-56 complex | Aerial mycelium: Light brownish gray, and hygroscopic. Positive utilization of arabinose, xylose, rhamnose, mannitol and inositol. |
| Streptosporangium violaceochromogenes MK-49[5] | Victomycin | Formation of spherical sporangium. Aerial mycelium: Shell pink. Positive utilization of xylose. Negative utilization of lactose. |
| Streptosporangium violaceochromogenes MK-78[6] | Platomycins | Formation of spherical sporangium. Aerial mycelium: White to pinkish white. Positive utilization of xylose. Negative utilization of lactose and glycerol. |

[1] K. Maeda, et al. (Institute Microbial Chemistry): Japan. Patent 34-2598, April 17, 1959.
[2] H. Umezawa, et al. New antibiotics, bleomycin A and B. J. Antibiotics 19: 200–209, 1966.
[3] The Upjohn Company: British Patent 1,277,150, June 7, 1972.
[4] T. Furumai, et al.: The antibiotic YA-56 complex: Taxonomy and production of the producing strain. J. Antibiotics 26: 70–76, 1973.
[5] I. Kawamoto, et al.: A new antibiotic victomycin (XK 49-1-B-2). J. Antibiotics 28: 358–371, 1975.
[6] T. Nara, et al. (kyowa-Hakko Kogyo Co., Ltd.): Japan. Kokai, 49-108292, October 15, 1974.

Taxonomic Classification

The actinomycetes strain E465-94 produced on agar media a cluster and sclerotium in the aerial mycelium which were morphologically typical of those found in some species of Streptomyces or Chainia. However, the amino acid and sugar composition of the cell-wall preparation of strain E465-94 was quite different from that of any species in the Family Streptomycetaceae. The cell-wall preparation contained meso-α-ε-diaminopimelic acid (meso-DAP) instead of LL-DAP which has been reported to be a specific cell-wall constituent of the genera Streptomyces and Chainia. Moreover, the major sugar components of the strain were galactose, mannose and rhamnose which are quite different than those reported for Streptomyces or Chainia. In view of the facts described above, it is proposed that a new genus Streptoalloteichus (Strepto-a Streptomyces - like organism, allo-altered and teichos-wall, i.e., a Streptomyces-like organisms with unusual cell-wall composition) be created under Family Streptomycetaceae in order to distinguish actinomycetes strains which resemble Streptomyces in morphology but have the cell-wall composition of strain E465-94 type; meso-DAP, alanine and glutamic acid as major amino acids and galactose, mannose and rhamnose as diagnostic neutral sugars. Thus, Streptoalloteichus is a sole genus among the genera of Family Streptomycetaceae which contains meso-DAP instead of LL-DAP in the cell-wall composition. It is also proposed that strain E465-94 be designated *Streptoalloteichus hindustanus* gen. nov. and sp. nov., because the organism was isolated from Northern India. Strain E465-94 appears clearly different from the microorganisms which have been reported to produce the bleomycins and bleomycin-related antibiotics.

It is to be understood that for the production of Bu-2231 the present invention, though described in detail with reference to the specific strain of *Streptoalloteichus hindustanus*, i.e. strain E465-94, A.T.C.C. 31158, is not limited to this microorganism or to microorganisms fully described by the cultural characteristics disclosed herein. It is intended that this invention also include other Bu-2231-producing strains or mutants of the said microorganism which can be produced by methods known in the art, for example, by subjecting the novel microorganism to x-ray or ultraviolet radiation, nitrogen mustard, phage exposure, and the like.

Preparation of the Antibiotics

Antibiotic complex Bu-2231 is produced by cultivating a Bu-2231-producing strain of *Streptoalloteichus hindustanus*, most preferably the strain *Streptoalloteichus hindustanus* E465-94, A.T.C.C. 31158, or a mutant thereof, under submerged aerobic conditions in an aqueous nutrient medium. The organism is grown in a nutrient medium containing an assimilable carbon source, for example an assimilable carbohydrate. Examples of suitable carbon sources include glucose, ribose, galactose, fructose, mannose, sucrose, lactose, soluble starch and glycerol. The nutrient medium should also contain an assimilable nitrogen source such as, for example, fish meal, soybean meal, corn steep liquor, peptones, meat extract, peanut flour, yeast extract or ammonium salts. In organic salts such as sodium chloride, potassium chloride, magnesium sulfate, calcium carbonate, phosphates, etc., are added if necessary. Trace elements such as copper, manganese, iron, zinc, etc. are added to the medium if desired or may be supplied as impurities of other constituents of the media. The incubation temperature may be any temperature at which a Bu-2231-producing strain is able to grow, e.g. 20°-54° C., but it is preferable to conduct the fermentation at 25°-35° C., especially at 27°-32° C. A neutral or near neutral initial pH, e.g., pH ~ 6-7, is preferably employed in the medium, and production of antibiotic is generally carried out for a period of from about 2-7 days. Ordinarily, optimum production is obtained in 3-5 days. For preparation of relatively small amounts, shake flasks and surface culture can be employed, but for the preparation of large amounts, submerged aerobic culture in sterile tanks is preferred. When tank fermentation is to be carried out, it is desirable to produce a vegetative inoculum in a nutrient broth by inoculating the broth culture with a spore from the organism and, when a young active vegetative inoculum has been obtained, transferring the inoculum aseptically to the fermentation tank medium. Aeration in tanks and bottles may be provided by forcing sterile air through or onto the surface of the fermenting medium. Further agitation in tanks is provided by a mechanical impeller. An antifoaming agent such as lard oil may be added as needed.

The production of Bu-2231 in the fermentation medium can readily be followed during the course of the fermentation by the paper disc-agar diffusion method using *Bacillus subtilis* PCI-219 and *Mycobacterium* 607 strain M6-3 as test organisms. Bu-2231 A and B as well as what are believed to be co-produced nebramycin factors are both active against *B. subtilis* PCI-219 but only the Bu-2231 A and B components showed activity against M. 607 M6-3. In the shake-flask fermentation, strain E465-94 produced 50-100 mcg./ml. of Bu2231 complex after 3-5 days.

Isolation and Purification of Bu-2231 Complex

After optimum broth potency has been obtained (as determined, for example, by the assay procedure mentioned above), the mycelium and undissolved residues are separated from the fermentation broth by conventional means such as filtration or centriguation. The antibiotic activity is contained in the filtrate and can be recovered therefrom by employing conventional adsorption techniques. The adsorbents which can be employed most advantageously in the recovery are the cationic exchange resins, for example, those resins of the IRC-50 type available commercially from Rohm and Hass Company under the Tradename "Amberlite IRC-50". The filtrate, neutralized if necessary to pH 7, is passed through a column packed with a cationic exchange resin such as Amberlite IRC-50 in the ammonium form. The resin is then washed with water. In addition to the Bu-2231 complex, the organism E465-94 also co-produces an aminoglycosides antibiotic complex comprised of nebramycin factors. This aminoglycoside impurity may be separated from the Bu-2231 complex of the present invention by elution with a dilute base, e.g. 0.25N ammonium hydroxide. The desired Bu-2231 complex which remains adsorbed on the resin may then be eluted with a mineral acid solution, e.g. pH 2 hydrochloric acid, and the Bu-2231 fractions of the eluate collected and combined.

Partial purification of the complex may be accomplished by chromotography of the combined Bu-2231 fractions over a suitable adsorbent such as activated carbon and elution with, for example, aqueous butanol at acid pH. The butanol layer is separated, and the aqueous layer is lyophilized or concentrated in vacuo to yield the solid Bu-2231 complex. The complex may be further subjected to chromotography and/or gel filtration to give the purified copper-containing solid complex.

Separation of Components Bu-2231 A and B

The glycopeptide components Bu-2231 A and B may be separated from the complex by gradient elution chromatography over a modified dextran derivative cationic ion exchanger, for example, a modified polysaccharide dextran of the type sold commercially under the tradename CM-Sephadex C-25. An aqueous solution of the Bu-2231 complex, preferably purified as described above, is added to a column containing the modified dextran ion exchanger As in the case of the bleomycins [*J. Antibiotics*, 19, 210–215 (1966)], it is easier to separate the components by this procedure if the complex is sufficiently chelated with copper. Thus, the preferred separation procedure involves dissolving the complex in a cupric chloride solution to ensure that it is in a difficult copper-chelated form and then applying this solution to the column. The components are then eluted in a stepwise manner with aqueous ammonium formate solution of concentrations varying from 1–7%. Bu-2231 B appears in the early fractions of eluate while later fractions contain Bu-2231 A. The fractions containing the same components are pooled, desalted by gel filtration, concentrated and lyophilized to give the purified Bu-2231 A and B components in their copper complex forms.

Use of ammonium formate as the eluant in the chromatographic separation procedure described above results in recovery of the lyophilized components in the form of formate salts. Standard procedures known to those skilled in the art may be used to convert the formate salts to the respective free bases and/or to convert the formate salts or free bases to other desired acid addition salts, e.g. the hydrochloride salts.

The glycopeptide components Bu-2231 A and B have the property of chelating with copper as do the bleomycins and thus, the components and their acid addition salts may exist either in the copper complex form or in the copper-free form. The copper-free forms of Bu-2231 A and B may be prepared from the copper complex forms by the use of $H_2S$ in methanol as described in U.S. Pat. No. 3,646,197.

The two glycopeptide antibiotic components may be differentiated from each other and the related bleomycins and phleomycins either in the copper complex or copper-free form by the TLC Systems S-102 and S-123 as shown below in Table 7.

Table 7.

| | Rf Values | |
|---|---|---|
| | S-102 | S-123 |
| Cu-A | 0.22 | 0.05 |
| Cu-B | 0.41 | 0.11 |
| Free A | 0.16 | 0.04 |
| Free B | 0.31 | 0.09 |
| Bleomycins | 0.34,0.44,0.69 | 0.21,0.50,0.79 |
| Phlemycins | 0.37,0.54,0.72 | 0.22,0.41,0.59 |

S-102: $SiO_2$ plate, $CH_3OH$-10% $CH_3COONH_4$ (1:1)
S-123: $SiO_2$ plate, $CH_3OH$-10% $CH_3COONH_4$-10% $NH_4OH$(10:9:1)

Characterization Data For Bu-2231 Antibiotic Components

The antibiotic substances Bu-2231 A and B are both amorphous bases which in the copper complex form appear as blue solids and in the copper-free form as white solids. Both substances are soluble in water and methanol, slightly soluble in ethanol and practically insoluble in other organic solvents.

Bu-2231 A and B are capable of forming salts with acids, and pharamceutically acceptable acid addition salts of the antibiotics are included within the present invention. Examples of suitable pharmaceutically acceptable acid addition salts include the non-toxic salt with organic and inorganic acids such as, for example, hydrochloric, sulfuric, phosphoric, acetic, formic, stearic, propionic, tartaric, maleic, benzoic, succinic and the like.

The elemental analyses of copper complex and copper-free Bu-2231 A and B were as follows:

Bu-2231 A (Cu-complex):
Calcd. $N,C_{64}H_{112}N_{20}O_{32}S_2Cu$: C,42.68; H,6.27; N,15.56; S,3.56. Found: C,42.66; H,6.16; N,15.31; S,31.4.
Bu-2231 A (Cu-free): Calcd. for $C_{64}H_{112}N_{20}O_{32}S_2$: C, 44.23; H, 6.50; N, 16.12; S, 3.69. Found: C, 45.10; H, 6.51; N, 16.05; S, 3.55.
Bu-2231 B (Cu-Complex): Calcd. for $C_{58}H_{100}N_{18}O_{31}S_2$·Cu: C, 41.63; H, 6.02; N, 15.07; S, 3.83. Found: C, 40.96; H, 5.61; N, 14.78; S, 3.39.
Bu-2231 B (Cu-free): Calcd. for $C_{58}H_{100}N_{18}O_{31}S_2$: C, 43.27; H, 6.26; N, 15.66; S, 3.98. Found: C, 43.01; H, 6.22; N, 14.81; S, 3.61.

The copper content in a combined sample of Bu-2231 A and B was determined to be about 3% by atomic absorption spectrometry.

The ultraviolet absorption maxima and optical rotation of the components are as follows:

| Compound | UV Absorption $\lambda_{max}^{2O}$ in m$\mu$ ($E_{1cm}^{1\%}$) | $[\alpha]_D^{23}$ (c 0.5,$H_2O$) |
|---|---|---|
| Bu-2231 A (Cu-complex) | 243(125),291 (98) | +50° |
| Bu-2231 A (Cu-free) | 235(sh),290 (67) | −21 |
| Bu-2231 B (Cu-complex) | 243(134),291 (109) | +76 |
| Bu-2231 B (Cu-free) | 235(sh),289.5 (77) | −19 |
| Bleomycin $A_2$ (Cu-complex) | 242(149),291 (121) | — |
| Phleomycin (Cu-complex) | 244(138),301 (49) | +84.5 (literature ref.) |

The ratio of UV absorbancies of the two absorption maxima for Bu-2231 (relative absorbancy at 240 m$\mu$ and 290 m$\mu$: 1.2–1.3) suggests the similarity of the new complex to the bleomycin group of antibiotics rather than the phleomycin group.

The infrared and nuclear magnetic resonance spectra for the copper-free hydrochloride salt of Bu-2231 A and the copper-free formate salt of Bu-2231 B are shown in FIGS. 1–4 of the drawings.

Both antibiotic components give positive reactions with ninhydrin reagent.

Structural Features of Bu-2231 Components

Close structural similarity of Bu-2231 A and B to bleomycin was indicated by the above-described physico-chemical properties. The copper-free preparation of the two components along with bleomycin $A_2$ were hydrolyzed in a sealed tube with 6N HCl for 20 hours at 105° C. Each of the hydrolyzates was examined comparatively by high-voltage paper electrophoresis. The location of the amino acids was detected by ninhydrin reagent and also by UV light.

As shown in Table 8, each of the six amino acids (I through VI) and one amine moiety (VII) of bleomycin $A_2$ reported in the literature (*J. Antibiotics* 21: 79, 1968)

was identified by paper electrophoresis. The hydrolysis products of Bu-2231 A and B showed the ninhydrin-positive zones corresponding to the amino acids I, II, Iv and V of bleomycin A₂, and the identity for each of the four amino acids isolated from Bu-2231 A and B with amino acids I, II, IV and V of bleomycin A₂ was established by chemical and spectral means. Amino acid III (zone at 13.5 cm.) of bleomycin A₂ was not present in Bu-2231 A and B, which instead showed an additional ninhydrin-positive zone at 14.8 cm. (designated as amino acid VIII). The structure of amino acid VIII has been determined as 4-amino-3-hydroxy-n-valeric acid which is a desmethyl analog of amino acid III.

Amino acid VI (zone at 8.5 cm., UV absorption maximum at 290 mμ.) of bleomycin A₂ was not present in Bu-2231 A and B. However, an acidic compound (IX) with a UV absorption maximum at 283 mμ. ($E_{1cm}^{1\%}$ 280) was isolated as a precipitate from the acid hydrolyzate of Bu-2231 A and B.

The terminal amine moiety (VII in Table 8) of bleomycin A₂ appeared at zone 31.5 cm. Bu-2231 A and B gave the same zone as amine VII of bleomycin A₂, but several amine moieties of bleomycin complex show similar mobility in this paper electrophoresis method. Subsequent analysis indicates in fact that the terminal amine moiety of Bu-2231 A and B is spermidine (X), the amine moiety of bleomycin A₅. Bu-2231 A gave an additional ninhydrin-positive zone at 23.0 cm. (XI in Table 8) which was absent in bleomycin A₂ and Bu-2231 B. Compound XI was identified as β-lysine.

The structures of the above-described amino acids and amine moieties are shown below:

Amine Acid and Amine Components of Bleomycin A₂ and Bu-2231 A and B

CH₃—CH—CH—COOH
    |    |
  OH  NH₂
L-threonine    I

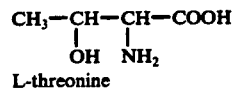
β-amino-β-(4-amino-6-carboxy-5-methyl-pyrimidine-2-yl)-propionic acid    II CH₃—CH—CH—CH—COOH
    |    |    |
  NH₂ OH CH₃
4-amino-3-hydroxy-2-methyl-n-valeric acid    III

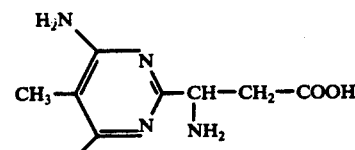
β-hydroxyhistidine    IV

NH₂—CH₂—CH—COOH
          |
         NH₂
L-β-aminoalanine    V

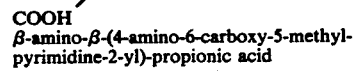
   VI

2'-(2-aminoethyl)-2,4'-bithiazole-4-carboxylic acid    VII

NH₂—(CH₂)₃—S⁺(CH₃)₂ . X⁻
3-aminopropyldimethylsulfonium salt    VIII

CH₃—CH—CH—CH₂—COOH
    |    |
  NH₂ OH
4-amino-3-hydroxy-n-valeric acid    IX structure unknown ($\lambda_{max}^{CH_3OH}$ 283 mμ)    X NH₂—(CH₂)₃—NH—(CH₂)₄—NH₂ (spermidine)    XI NH₂—(CH₂)₃—CH—CH₂—COOH (β-lysine)
           |
          NH₂

The sugar component of Bu-2231 A and B was also investigated comparatively with bleomycin. A mixture of components A and B was refluxed in methanol with a strongly acidic resin (Amberlyst 15) for 20 hours. Basic fragments from the hydrolysis were adsorbed on the resin and neutral products liberated in the solution were concentrated in vacuo to a sticky syrup. This material was trimethylsilyated and then subjected to gas-chromatographic analysis. Bleomycin gave peaks assignable to gulose and mannose, and the Bu-2231 components showed nearly the same elution pattern as that of bleomycin, indicating the same structure of the carbohydrate portion in the antibiotics.

Table 8.

| Paper Electrophoresis of Acid Hydrolysis Products | | | |
|---|---|---|---|
| | location of ninhydrin-positive zone (distance from the origin)** | | |
| Amino Acids & Amine* | Bleomycin A₂ | Bu-2231 A | Bu-2231 B |
| VI | 8.5 cm | — | — |
| I | 9.7 | 9.7 | 9.7 |
| II | 12.0 | 12.0 | 12.0 |
| III | 13.5 | — | — |
| VIII | — | 14.8 | 14.8 |
| IV | 16.0 | 16.0 | 16.0 |
| V | 18.5 | 18.5 | 18.5 |
| XI | — | 23.0 | — |
| VII (X) | 31.5 | 31.5 | 31.5 |

*Structures of the amino acid and amine components are shown in the text.
**Toyo filter paper No. 51, buffer solution: formic acid-acetic acid-water (25:75:900).

Antimicrobial Activity

The minimum inhibitory concentrations (MIC) of Bu-2231 A and B were determined against a wide variety of bacteria and fungi by the two-fold agar dilution method. Mueller-Hinton agar medium was used for the determination of bacterial MIC's (gram-positive and gram-negative), Medium #1001 [Glycerol (3%). Na-glutamate (0.3%), peptone (0.2%), Na₂HPO₄ (0.31%), KH₂PO₄ (0.1%), ammonium citrate (0.005%), MgSO₄.7H₂O (0.001%), agar (1.5%)] for acid-fast bacteria and sabouraud agar for fungi. The results are shown in Tables 9 and 10 comparatively with bleomycin and phleomycin. The antibacterial and antifungal activities of Bu-2231 A and B are much higher than those of the reference antibiotics. Bu-2231 A showed somewhat greater antibacterial activity than Bu-2231 B, but was less potent than the latter in antifungal activity.

Table 9.

| | Antibacterial spectra of Bu-2231 A and B | | | | Bleo-mycin | Phleomycin |
|---|---|---|---|---|---|---|
| | Bu-2231 A | | Bu-2231 B | | | |
| test organism | Cu-free | Cu-complex | Cu-free | Cu-complex | NIHJ | #616 |
| gram-negative | | | | | | |
| E. coli NIHJ | 0.025 | 0.025 | 0.1 | 0.1 | 0.8 | 0.8 |
| " Juhl A15119 | 0.1 | 0.1 | 0.2 | 0.2 | 1.6 | 1.6 |
| " K-12 A9632 | 0.05 | 0.05 | 0.1 | 0.2 | 0.8 | 1.6 |
| " A20665 | 0.05 | 0.05 | 0.05 | 0.25 | 0.2 | 0.4 |
| " A20683 | 6.3 | 25 | 12.5 | 50 | >100 | >100 |
| " A20732 | 0.05 | 0.05 | 0.2 | 0.1 | 1.6 | 1.6 |
| E. cloacae A21006 | 1.6 | 1.6 | 6.3 | 12.5 | >100 | 50 |
| K. pneumoniae D11 | <0.0063 | 0.0125 | 0.025 | <0.0063 | 0.2 | 0.4 |
| " A9678 | 0.2 | 0.4 | 0.4 | 0.4 | 6.3 | 12.5 |
| " A20680 | 6.3 | 50 | 25 | 100 | >100 | >100 |
| " A20328 | 0.8 | 0.8 | 1.6 | 1.6 | 25 | >100 |
| P. vulgaris A9436 | 0.2 | 0.4 | 0.2 | 0.2 | 6.3 | 0.8 |
| P. morganii A9553 | 0.4 | 0.4 | 1.6 | 1.6 | >100 | 6.3 |
| P. mirabilis A9554 | 0.1 | 0.1 | 0.2 | 0.2 | 50 | 1.6 |
| P. rettgeri A15167 | 0.4 | 0.4 | 0.8 | 0.8 | >100 | 3.1 |
| P. stuartii A20894 | 0.4 | 0.4 | 0.4 | 0.8 | 3.1 | 0.8 |
| " A20734 | 0.4 | 0.4 | 0.8 | 0.8 | >100 | 1.6 |
| S. marcescens A20019 | 0.4 | 0.4 | 0.8 | 0.8 | >100 | 0.8 |
| " A20460 | 0.4 | 0.4 | 0.8 | 0.8 | >100 | 0.8 |
| " A20333 | 0.2 | 0.2 | 0.8 | 0.4 | >100 | 0.8 |
| " A21235 | 0.2 | 0.4 | 1.6 | 1.6 | 100 | 0.8 |
| P. aeruginosa A 9923 | 50 | 100 | >100 | >100 | >100 | >100 |
| " A9930 | 0.4 | 0.4 | 0.8 1.6 | >100 | 3.1 | |
| " H9, D113 | >100 | >100 | >100 | >100 | >100 | >100 |
| " A20741 | 0.2 | 0.2 | 0.2 | 0.2 | 12.5 | 6.3 |
| gram-positive | | | | | | |
| S. aureus 209P | 0.1 | 0.2 | 0.4 | 0.4 | 6.3 | 0.2 |
| " Smith A9537 | 0.1 | 0.1 | 0.05 | 0.05 | 3.1 | 0.1 |
| " #193 | 0.1 | 0.2 | 0.4 | 0.4 | 12.5 | 0.2 |
| " 209P, R4 | 0.4 | 0.4 | 0.8 | 0.8 | 12.5 | 0.4 |
| " A20239 | 0.2 | 0.2 | 0.8 | 0.8 | 12.5 | 0.4 |
| " BX-1633,A9606 | 0.2 | 0.2 | 0.8 | 0.2 | 6.3 | 0.4 |
| S. lutea PCI-1001 | 0.2 | 0.2 | 0.4 | 0.8 | 100 | 0.4 |
| M. flavus D12 | 0.2 | 0.2 | 0.4 | 0.8 | 50 | 0.2 |
| B. mycoides "0" | 0.2 | 0.1 | 0.2 | 0.2 | 12.5 | 0.2 |
| B. sphaericus #122 | <0.0063 | <0.0063 | 0.2 | 0.2 | 6.3 | 0.4 |
| B. cereus ATCC 10702A | 0.2 | 0.2 | 0.2 | 0.1 | 1.6 | 0.2 |
| B. subtilis PCI-219 | <0.0063 | <0.0063 | <0.0063 | <0.0063 | <0.0063 | <0.0063 |
| B. anthracis 115 | 0.05 | 0.05 | 0.1 | 0.2 | 12.5 | 0.4 |
| acid-fast | | | | | | |
| Mycobacterium 607, D87 | 0.2 | 0.1 | 0.1 | 0.05 | 0.8 | 0.4 |
| " 607, D46 | 0.1 | 0.1 | 0.1 | 0.05 | 0.2 | 0.2 |
| " 607, D47 | 0.1 | 0.1 | 0.05 | 0.025 | 0.4 | 0.2 |
| " phlei, D88 | 0.05 | 0.05 | 0.05 | 0.025 | 0.2 | 0.1 |
| " ranae, ATCC110 | 0.1 | 0.1 | 0.1 | 0.05 | 0.8 | 0.4 |

Table 10.

| BBRI Code # | test organism | Antifungal spectrum of Bu-2231 A and B | | | | Bleomycin NIHJ | Phleomycin #616 |
|---|---|---|---|---|---|---|---|
| | | Bu-2231 A | | Bu-2231 B | | | |
| | | Cu-free | Cu-complex | Cu-free | Cu-complex | | |
| Ca-1 | C. albicans IAM 4888 | 0.8 | 1.6 | 0.8 | 0.8 | 12.5 | 3.1 |
| Ca-2 | " Nystatin-R | 0.8 | 1.6 | 0.8 | 0.8 | 12.5 | 1.6 |
| Ca-4 | " #520 Yale A9540 | 3.1 | 6.3 | 1.6 | 3.1 | >100 | 6.3 |
| Ck-1 | C. krusei IAM 4489 | 0.8 | 0.8 | 0.4 | 0.2 | 12.5 | 0.8 |
| Ck-2 | " #96 A15052 | 0.8 | 0.8 | 0.4 | 0.2 | 3.1 | 0.8 |
| Ct-1 | C. tropicalis IAM 4157 | 0.8 | 1.6 | 0.8 | 0.8 | 12.5 | 3.1 |
| Ct-4 | " #125 A15051 | 0.8 | 1.6 | 0.8 | 0.8 | >100 | 6.3 |
| Cn-1 | C. neoformans | 0.4 | 0.2 | 0.2 | 0.1 | 1.6 | 0.4 |
| Cn-2 | " IAM 4514 | 0.4 | 0.2 | 0.2 | 0.1 | 1.6 | 0.4 |
| Sc-1 | S. cerevisiae ATCC 9763 | 0.4 | 0.2 | 0.2 | 0.1 | 0.8 | 0.8 |
| Sc-2 | " IAM 4009 | 0.4 | 0.2 | 0.2 | 0.1 | 0.4 | 0.8 |
| An-1 | A. niger var Tieghem | 0.2 | 0.2 | 0.2 | 0.2 | 0.4 | 0.4 |
| Af-1 | A. fumigatus IAM 2530 | 0.8 | 0.4 | 0.4 | 0.2 | 0.8 | 0.8 |
| Hy-1 | Hormodendrum sp. | 0.8 | 0.2 | 0.2 | 0.2 | 0.8 | 0.8 |
| Sy-1 | Sporotrichum sp. | 3.1 | 3.1 | 3.1 | 1.6 | >100 | 12.5 |
| Vx-1 | Verticillium sp. | 3.1 | 6.3 | 1.6 | 3.1 | 6.3 | 6.3 |
| My-1 | Mucor sp. | 6.3 | 6.3 | 3.1 | 3.1 | 3.1 | 3.1 |
| Fm-1 | F. moniliforme NRRL A2284 | 0.8 | 0.8 | 0.8 | 0.8 | >100 | 12.5 |
| Cl-1 | C. lunata ATCC 13432 | 0.8 | 0.2 | 0.2 | 0.2 | 0.1 | 0.4 |
| Pt-1 | P. citrinum IAM 7008 | 1.6 | 1.6 | 1.6 | 0.8 | >100 | 3.1 |
| Tm-1 | T. mentagrophytes D-155 | 12.5 | 12.5 | 6.3 | 6.3 | >100 | 12.5 |
| Ta-1 | T. asteroides | 3.1 | 1.6 | 0.8 | 1.6 | >100 | 6.3 |
| Tr-1 | T. rubrum D-55 | 3.1 | 1.6 | 0.8 | 1.6 | >100 | 3.1 |
| Mc-1 | M. canis D-51 | 3.1 | 1.6 | 0.8 | 1.6 | >100 | 6.3 |

The in vivo activity of Bu-2231 complex was evaluated in experimental mice infections against S. aureus Smith and E. coli NIHJ. Bleomycin was tested comparatively as a reference antibiotic. The results are shown in Table 11. Bu-2231 was about 20-fold (S. aureus) to 80-fold (E. coli) more active than bleomycin in terms of median protective dose ($PD_{50}$) value.

Table 11.

| | In vivo activity of Bu-2231 vs. S. aureus Smith infection | |
|---|---|---|
| dose (sc) | Bu-2231 (A + B) | Bleomycin |
| 8 mg/kg | — | 4/5 |
| 4 | — | — |
| 2 | — | 2/5 |
| 1 | 5/5 | — |
| 0.5 | 5/5 | 1/5 |
| 0.25 | 5/5 | — |
| 0.13 | 1/5 | 0/5 |
| 0.06 | 1/5 | — |
| 0.03 | 0/5 | — |
| $PD_{50}$ | 0.14 mg/kg | 2.5 mg/kg |
| 8 mg/kg | — | 5/5 |
| 2 | 5/5 | 1/5 |
| 0.5 | 5/5 | 1/5 |
| 0.13 | 5/5 | 0/5 |
| 0.03 | 2/5 | — |
| 0.008 | 1/5 | — |
| $PD_{50}$ | 0.031 mg/kg | 2.55 mg/kg |

The in vivo activty of the individual components of Bu-2231 in each of the copper-free and copper complex forms was also determined in E. coli infection. As shown in Table 12, Bu-2231 A was somewhat more active than Bu-2231 B. The presence of copper in the Bu-2231 molecule did not affect the in vivo activity appreciably.

Table 12.

| | In vivo Activity of Bu-2231 A and B in Cu-free and Cu-complex forms (vs. E. coli NIHJ infection) | | | |
|---|---|---|---|---|
| | Bu-2231 A | | Bu-2231 B | |
| dose (sc) | Cu-free | Cu-complex | Cu-free | Cu-complex |
| 8 | — | 5/5 | — | 3/5 |
| 2 | 5/5 | 5/5 | 5/5 | 5/5 |
| 0.5 | 5/5 | 5/5 | 5/5 | 5/5 |
| 0.13 | 5/5 | 4/5 | 4/5 | 3/5 |
| 0.03 | 3/5 | 3/5 | 1/5 | 2/5 |
| 0.008 | 1/5 | 0/5 | 0/5 | 2/5 |
| $PD_{50}$ | 0.024 mg/kg | 0.031 mg/kg | 0.065 mg/kg | 0.040 mg/kg |

The acute toxicity of copper-free Bu-2231 A and B was determined in mice by a single subcutaneous injection. Groups of 3 mice were used for each dose level and the body weight was recorded for 16 days. The results ae shown in Table 13. Bu-2231 A was somewhat more toxic than Bu-2231 B. No death occurred with Bu-2231 B up to a dose of 50 mg./kg. but loss of body weight was noted in all the animals tested.

Table 13.

| | | Acute toxicity of Bu-2231 | | | | | | | | | |
|---|---|---|---|---|---|---|---|---|---|---|---|
| | | No. of survivors at day | | | | | Mean body weight (gr) | | | | |
| | dose (sc) | 0 | 4 | 5 | 9 | 12 | 16 | 0 | 4 | 10 | 16 | $LD_{50}$ |
| Bu-2231 A Cu-free | 50 mg/kg | 3 | 2 | 1 | 0 | 0 | 0 | 19.3 | 15.0 | — | — | |
| | 25 | 3 | 3 | 3 | 3 | 2 | 2 | 20.0 | 14.7 | 13.3 | 14.5 | 28 mg/kg |
| | 12.5 | 3 | 3 | 3 | 3 | 3 | 3 | 20.0 | 16.7 | 15.7 | 16.3 | |
| | 6.3 | 3 | 3 | 3 | 3 | 3 | 3 | 20.0 | 18.7 | 17.3 | 19.3 | |
| Bu-2231 B Cu-free | 50 mg/kg | 3 | 3 | 3 | 3 | 3 | 3 | 19.3 | 15.7 | 14.7 | 15.3 | |
| | 25 | 3 | 3 | 3 | 3 | 3 | 3 | 18.7 | 15.7 | 16.7 | 17.3 | >50 mg/kg |
| | 12.5 | 3 | 3 | 3 | 3 | 3 | 3 | 20.0 | 16.7 | 19.3 | 20.7 | |
| | 6.3 | 3 | 3 | 3 | 3 | 3 | 3 | 18.7 | 16.0 | 18.7 | 20.3 | |

Antitumor Activity

In addition to the antimicrobial activity shown above, Bu-2231 complex and its major components Bu-2231 A and B have also been found to inhibit various experimental animal tumors. Tests conducted on two transplanted rodent tumor systems, Walker 256 carcinosarcoma in ascitic form and Lewis Lung carcinoma with intraperitoneal tumor brei implant, are described below. The methodology used followed in general the protocols of the National Concer Institute as reported in *Cancer Chemotheraphy Reports:* 3(2):1-103 (1972). The essential details of the experiments are provided in Tables I-III below.

Table I.

| | Effect of Bu-2231 on Walker 256 Ascitic Tumor Exp. #5439 | | | | | |
|---|---|---|---|---|---|---|
| | | | Effect | Average | Survivors | |
| Material | Dose mcg/kg/day | MST Days | MST %T/C | Weight Change/g. | Day 5 | Day 44 |
| Bleomycin | 2560 | >44.0 | >489 | +10 | 6/6 | 4/6 |
| | 640 | 17.5 | 194 | +9 | 6/6 | 1/6 |
| | 160 | 10.0 | 111 | +11 | 6/6 | 0/6 |
| Bu-2231 | 2560 | 26.0 | 288 | +7.5 | 6/6 | 0/6 |
| | 640 | >44.0 | 489 | +18 | 6/6 | 5/6 |
| | 160 | >44.0 | >489 | +19 | 6/6 | 4/6 |
| | 40 | 9.0 | 100 | +19.5 | 6/6 | 1/6 |
| | 10 | 8.5 | 94 | +18 | 6/6 | 1/6 |
| Control-saline | | 9.0 | — | +34 | 10/10 | 0/10 |

| | |
|---|---|
| Tumor: | $10^6$ ascitic cells implanted ip into female SD rats |
| Treatment: | Once daily ip for 8 days starting Day 1 |
| Evaluation: | MST=Median survival time in days |
| Effect: | %T/C=MST treated/MST control X100 |
| Criteria: | T/C ≥ 125 considered significant tumor inhibition (prolongation of host survival) |
| Survivors: | Day 5 toxicity evaluation, weight change recorded Day 44 Experiment terminated, survivors considered "cured." Others died of tumor. |

Table II.

Effect of Bu-2231 Fractions on Walker 256 Ascitic Tumor Exp. #5501

| Material | Dose mcg/kg/day | MST Days | Effect MST %T/C | Average Weight Change/g. | Survivors Day 5 |
|---|---|---|---|---|---|
| Bleomycin | 640 | 12.5 | 179 | + 4.5 | 6/6 |
|  | 160 | 11.0 | 157 | + 7.8 | 6/6 |
| Bu-2231 A | 640 | 17.5 | 250 | + 7.2 | 6/6 |
|  | 160 | 12.5 | 179 | +28.8 | 6/6 |
|  | 40 | 11.0 | 157 | + 6.0 | 6/6 |
|  | 10 | 9.0 | 129 | + 5.5 | 6/6 |
| Bu-2231 B | 640 | 13.0 | 186 | +10.7 | 6/6 |
|  | 160 | 13.0 | 186 | +36.5 | 6/6 |
|  | 40 | 11.0 | 157 | + 8.3 | 6/6 |
|  | 10 | 8.0 | 114 | +36.5 | 6/6 |
| Control-saline |  | 7.0 | — | +38.4 | 10/10 |

| | |
|---|---|
| Tumor: | 10$^6$ scitic cells implanted ip into female SD rats |
| Treatment: | Once daily ip for 8 days starting Day 1 |
| Evaluation: | MST = Median survival time in days |
| Effect: | %T/C = MST treated /MST control X100 |
| Criteria: | T/C≧125 considered significant tumor inhibition (prolongation of host survival) |
| Survivors: | Day 5 toxicity evaluation, weight change recorded |

Table III.

Effect of Bu-2231 Fractions on Lewis Lung Carcinoma Exp. #55

| Material | Dose mg/kg/day | MST Days | Effect MST %T/C | Average Weight Change/g. | Survivors Day 5 |
|---|---|---|---|---|---|
| Bleomycin | 8 | 10.5 | 48 | − 1.1 | 6/6 |
|  | 4 | 12.5 | 57 | − 2.3 | 6/6 |
|  | 2 | 24.0 | 109 | − 1.5 | 6/6 |
|  | 1 | 24.0 | 109 | − 1.3 | 6/6 |
| Bu-2231 A | 8 | 6.0 | 27 | − 3.3 | 6/6 |
|  | 4 | 7.0 | 32 | − 3.1 | 6/6 |
|  | 2 | 25.0 | 114 | − 1.3 | 6/6 |
|  | 1 | 27.0 | 123 | − 2.3 | 6/6 |
|  | 0.5 | 26.5 | 120 | − 1.1 | 6/6 |
| Bu-2231 B | 8 | 6.0 | 27 | − 1.8 | 5/6 |
|  | 4 | 10.5 | 48 | − 1.4 | 6/6 |
|  | 2 | 30.0 | 136 | − 1.8 | 6/6 |
|  | 1 | 29.5 | 134 | − 0.8 | 6/6 |
|  | 0.5 | 22.5 | 102 | − 1.1 | 6/6 |
| Control-saline | — | 22.0 | — | − 0.8 | 10/10 |

| | |
|---|---|
| Tumor: | 2 × 10$^6$ cells from minced tumor brei implanted ip into male C57 B1/6 mice |
| Treatment: | Once daily, ip, for 9 days starting Day 1 |
| Evaluation: | MST = Median survival time in days |
| Effect: | %T/C = MST treated/MST control X100 |
| Criteria: | T/C ≦ 125 considered significant tumor inhibition (prolongation of host survival) |
| Survivors: | Day 5 toxicity evaluation, weight change recorded |

The results shown in the tables are intrepreted as follows:

TABLE I

Tests were conducted on Walker 256 ascitic tumor with Bu-2231 complex and with bleomycin complex as a control. The dose of 2560 mcg./kg. is active but toxic since the I/C was lower than the next lower dose and no long term (44 day) survivors were observed. The minimum effective dose (MED) of bleomycin was 640 mcg./kg. whereas the MED of Bu-2231 was 160 mcg./kg., indicating that Bu-2231 is about 4 times as potent as bleomycin.

TABLE II

Bu-2231 A and B in the form of their copper-free formate salts were tested on Walker 256 ascitic tumor. The probable minimum effective dose (MED) is 160 mcg./kg. in this experiment. Comparable survival increase (T/C=157) was seen with both components at 40 mcg./kg., thus indicating 4 fold greater potency for Bu-2231 A and B. The A component may be slightly more potent than the B (activity at 10 mcg./kg.), but the difference cannot be considered significant.

TABLE III

Bleomcyin shows very borderline effects occasionally in tests against Lewis Lung Carcinoma. In this experiment Bu-2231 A was just below an active level at 1 mg./kg. (T/C=123) while Bu-2231 B was active at doses of 2 and 1 mg./kg.

The following examples are offered only for the purposes of illustrating the present invention and are not intended to limit same in any respect. CM-Sephadex C-25 is a tradename for a dry insoluble powder, (manufactured by Pharmacia Fine Chemicals Inc.) composed of microscopic beads which are synthetic organic compounds containing carboxymethyl functional groups and which are derived from polysaccharide dextran. Amberlyst 15 is a tradename for an ion-exchange resin manufactured by Rohm & Haas Company. Amberlite XAD-2 is a trademark for an adsorbent resin composed of styrenedivinylbenzene copolymer, manufactured by Rohm & Haas Company.

EXAMPLE 1

Fermentation of Complex

A well-grown agar slant of the Bu-2231 producing organism, E465-94, was used to inoculate liquid vegetative medium containing the following ingredients: 1.5% glucose, 0.5% polypeptone, 0.2% yeast extract, 0.05% $K_2HPO_4$ and 0.05% $MgSO_4.7H_2O$. The seed culture was incubated at 28° C. for 2 days on a rotary shaker (250 rpm), at 2 ml. of the growth was transferred to 100 ml. of the fermentation medium in a 500-ml. Erlenmeyer flask which had a composition of 2% glycerol, 1% pharmamedia, 1% cornsteep liquor, 0.3% $(NH_4)_2SO_4$, 0.003% $ZnSO_4.7H_2O$ and 0.4% $CaCO_3$. Antibiotic production reached a maximum after 3-5 days shaking at 38° C.

EXAMPLE 2

Extraction and Purification

The harvested broth (ca 10L, 50 mcg./ml.) produced according to Example 1 was filtered and the bioactivity in the filtrate was adsorbed at pH 7 by Amberlite IRC-50 ($NH_4^{30}$ form, 900 ml.). The resin was washed with water (5L) and subsequently with 0.25N $NH_4OH$ solution (4L) to elute nebramycin factors. Bu-2231 complex was then eluted from the resin with HCl solution (1L × 3) at pH 2. The Bu-2231 fractions were combined, adsorbed by carbon (30 g.) and eluted with aqueous butanol (1L × 3) at pH 2. The butanol layer was separated and the aqueous layer was concentrated in vacuo to dryness. The crude solid thus obtained (1.2 g.) was purified by Amberlite XAD-2 chromatography and then by Sephadex LH-20 chromatograhy to give a faint greenish powder of Bu-2231 complex (150 mg., copper complex form).

EXAMPLE 3

Separation of Components

For the separation of each component, Bu-2231 complex (140 mg.) was dissolved in 3 ml. of 0.7% cupric chloride solution and applied to a column of CM-Sephadex C-25 (85 ml.) which was eluted gradiently with aqueous ammonium formate solution of 1%-7%. Bu-2231 B was eluted with 3% ammonium formate solution and Bu-2231 A at 5% concentration. Each fraction was desalted by Sephadex LH-20 chromatography, concentrated in vacuo and lyophilized to give the respective formate salts of Bu-2231 A (84 mg.) and B (21 mg.) (copper-complex forms). The copper-free formate salt preparations were obtained by treating the copper complex forms with $H_2S$ in methanol according to the general procedure of Example 1 of U.S. Pat. No. 3,646,197.

EXAMPLE 4
Bu-2231 A Hydrochloride Salt

A solution of copper-free Bu-2231 A formate (750 mg.) in 100 ml. of methanol was adjusted to pH 2.0 with an addition of 2N methanolic hydrogen chloride solution. The solution was then added dropwise to 300 ml. of acetone with stirring. The precipitate which formed was separated by filtration and dried in vacuo to give the crude Bu-2231 A hydrochloride salt as a white powder (673 mg.). A portion of this powder (140 mg.) was applied to a column containing 70 ml. of Sephadex LH-20 (tradename for a modified alkylated dextran gel distributed by Pharmacia Fine Chemicals Inc.) packed in 98% methanol. The column was developed by 98% methanol and the bioactive fractions then collected, concentraed in vacuo and lyophilized to give the copper-free hydrochloride of Bu-2231 A (105 mg.).

We claim:

1. The glycopeptide antitiotic Bu-2231 A or a pharmaceutically acceptable acid addition salt thereof; which antibiotic substance is a base capable of existing in both a copper complex form and a copper-free form; which when subjected to acid hydrolysis gives the amino acids L-threonine, $\beta$-amino-$\beta$-(4-amino-6-carboxy-5-methylpyrimidine-2-yl)propionic acid, $\beta$-hydroxyhistidine, L-$\beta$-aminoalanine, 4-amino-3-hyroxy-n-valeric acid, $\beta$-lysine and an amino acid exhibiting an ultraviolet absorption maximum at 283 m$\mu$($E_{1cm}^{1\%}$ 280), the terminal amine spermidine and the carbohydrates mannose and gulose; which in the copper complex form (1) is a bluish amorphous solid soluble in water and methanol, slightly soluble in ethanol and practically insoluble in other organic solvents, (2) gives a positive reaction with ninhydrin, (3) has the following elemental analysis (percent): C, 42.66; H, 6.16; N, 15.31; and S, 3.14, (4) shows ultraviolet absorption $\lambda_{MAX}^{H_2O}$ 243 and 291 m$\mu$ ($E_{1cm}^{1\%}$ 125 and 98), (5) has a specific rotation of $[\alpha]_D^{23} = +50°$ (c, 0.5, $H_2O$), and (6) exhibits an Rf of 0.22 in thin layer chromatography using silica gel and methanol—10% ammonium acetate (1:1) and an Rf of 0.05 using silica gel and methanol-10% ammonium acetate-10% ammonium hydroxide (10:9:1), which in the copper-free form (1) is a white amorphous solid, (2) has a specific rotation of $[\alpha]_D^{23} = -21°$ (c, 0.5, $H_2O$), (3) has the following elemental analysis (percent): C, 45.10; H, 6.51; N, 16.05; and S, 3.55, (4) shows ultraviolet absorption $\lambda_{MAX}^{H_2O}$ 235 and 290 m$\mu$ ($E_{1cm}^{1\%}$ sh and 67), and (5) exhibits an Rf of 0.16 in thin layer chromatography using silica gel and methanol — 10% ammonium formate (1:1) and an Rf of 0.04 using silica gel and methanol— 10% ammonium acetate — 10% ammonium hydroxide (10:9:1); which as the copper-free hydrochloride salt when pelleted in potassium bromide has an infrared spectrum substantially as shown in FIG. 1 and when dissolved in deuterium oxide at a concentration of 10% gives an NMR spectrum substantially as shown in FIG. 2; and which in both the copper-free and copper complex forms is effective in inhibiting the growth of bacteria and fungi.

2. The free base of Bu-2231 A as defined in claim 1.
3. A pharmaceutically acceptable acid addition salt of Bu-2231 A as defined in claim 1.
4. The formate salt of Bu-2231 A as defined in claim 1.
5. The hydrochloride salt of Bu-2231 A as defined in claim 1.
6. The glycopeptide antibiotic Bu-2231 B or a pharmaceutically acceptable acid addition salt thereof; which antibiotic substance is a base capable of existing in both a copper complex form and a copper-free form; which when subjected to acid hydrolysis gives the amino acids L-threonine, $\beta$-amino-$\beta$-(4-amino-6-carboxy-5-methylpyrimidine-2-yl)propionic acid, $\beta$-hydroxyhistidine, L-$\beta$-aminoalanine, 4-amino-3-hydroxy-n-valeric acid and an amino acid exhibiting an ultraviolet absorption maximum at 283 m$\mu$ ($E_{1cm}^{1\%}$ 280), the terminal amine spermidine and the carbohydrates mannose and gulose; which in the copper complex form (1) is a bluish amorphous solid soluble in water and methanol, slightly soluble in ethanol and practically insoluble in other organic solvents, (2) gives a positive reaction with ninhydrin, (3) has the following elemental analysis (percent): C, 40.96 H, 5.61; N, 14.78; and S, 3.39, (4) shows ultraviolet absortpion $\lambda_{Max}^{H_2O}$ 243 and 291 mu ($E_{1cm}^{1\%}$ 134 and 109), (5) has a specific rotation of $[\alpha]_D^{23} = +76°$ (c, 0.5, $H_2O$) and (6) exhibits an Rf of 0.41 in thin layer chromatography using silica gel and methanol — 10% ammonium acetate (1:1) and an Rf of 0.11 using silica gel and methanol — 10% ammonium acetate — 10% ammonium hydroxide (10:9:1), which in the copper-free form (1) is a white amorphous solid; (2) has a specific rotation of $[\alpha]_D^{23} = -19°$ (c, 0.5, $H_2O$), (3) has the following elemental analysis (percent): C, 43.01; H, 6.22; N, 14.81 and s, 3.61, (4) shows ultraviolet absorption $\lambda_{MAX}^{H_2O}$ 235 and 289.5 m$\mu$ ($E_{1cm}^{1\%}$ sh and 77) and (5) exhibits an Rf of 0.31 in thin layer chromatography using silica gel and methanol — 10% ammonium formate (1:1) and an Rf of 0.09 using silica gel and methanol — 10% ammonium acetate — 10% ammonium hydroxide (10:9:1); which as the copper-free formate salt when pelleted in potassium bromide has an infrared spectrum substantially as shown in FIG. 3 and when dissolved in deuterium oxide at a concentration of 10% gives an NMR spectrum substantially as shown in FIG. 4; and which in both the copper-free and copper complex forms is effective in inhibiting the growth of bacteria and fungi.

7. The free base of Bu-2231 B as defined in claim 6.
8. A pharmaceutically acceptable acid addition salt of Bu-2231 B as defined in claim 6.
9. The formate salt of Bu-2231 B as defined in claim 6.
10. The hydrochloride salt of Bu-2231 B as defined in claim 6.
11. A process for producing the antibiotic complex Bu-2231 which comprises cultivating *Streptoalloteichus hindustanus* A.T.C.C. 31158 in an aqueous nutrient medium containing assimilable sources of nitrogen and carbon under submerged aerobic conditions until a substantial amount of Bu-2231 complex is produced by said organism in said culture medium.
12. The process of claim 11 which includes the further step of recovering the Bu-2231 complex from the culture medium by (a) separating the water-soluble antibiotic complex from the mycelium, (b) absorbing the complex on a cationic exchange resin, (c) separating the co-produced aminoglycoside complex from the desired glycopeptide Bu-2231 complex by eluting the adsorbed complex with a dilute aqueous base until the aminoglycoside complex is selectively eluted from the adsorbent, and (d) eluting the Bu-2231 complex from the adsorbent with a mineral acid solution.

13. A method for obtaining as separate substances antibiotic Bu-2231A as defined in claim 1 and antibiotic Bu-2231B as defined in claim 6, which comprises cultivating Streptoalloteichus hindustanus A.T.C.C. 31158 in an aqueous nutrient medium containing assimilable sources of nitrogen and carbon under submerged aerobic conditions until a substantial amount of Bu-2231 complex is produced by said organism in said culture medium, recovering the Bu-2231 complex from the culture medium, absorbing the complex upon a modified polysaccharaide dextran derivative cationic exchanger containing carboxymethyl functional groups and fractionally eluting the separate Bu-2231A and B components in their copper complex forms with aqueous ammonium formate in concentrations increasing successively from 1 to 7%.

14. The process according to claim 13 wherein the Bu-2231 complex is dissolved in cupric chloride solution before being absorbed upon the ion exchange resin.

15. The process according to claim 13 which includes the further step of treating the copper complex forms of Bu-2231A and B with hydrogen sulfide in methanol to produce the corresponding copper-free forms.

* * * * *